United States Patent [19]

Gröninger

[11] 4,083,030

[45] Apr. 4, 1978

[54] ELECTRIC HYGROMETER

[75] Inventor: Markus Gröninger, Neuenhof, Switzerland

[73] Assignee: Howag AG, Wohlen, Switzerland

[21] Appl. No.: 732,391

[22] Filed: Oct. 14, 1976

[30] Foreign Application Priority Data

Oct. 15, 1975 Switzerland .............. 13348/75

[51] Int. Cl.² .................................... H01L 7/00
[52] U.S. Cl. ................................... 338/35; 23/254 E; 200/61.06
[58] Field of Search ............... 338/35, 34; 23/254 E, 23/255 E; 73/336.5, 335, 336, 23, 27; 200/61.06, 61.04

[56] References Cited

U.S. PATENT DOCUMENTS

| 2,445,073 | 7/1948 | Marette et al. ............ 338/34 |
| 3,255,324 | 6/1966 | Ovshinsky ............ 338/34 X |

Primary Examiner—C. L. Albritton
Attorney, Agent, or Firm—Peter K. Kontler

[57] ABSTRACT

An electric hygrometer wherein a body of viscous hygroscopic electrolyte is supported exclusively by two or more spaced-apart carriers so that the electrolyte contacts the gaseous medium whose relative humidity requires determination and is in conductive contact with two conductors. The impedance between the conductors varies with relative humidity of the medium. The carriers may consist of conductive and/or insulating material; in each instance, the carriers may constitute spheres, straight wires, U-shaped or V-shaped wires, loops, open or closed rings or other configurations. If the electrolyte is supported by two carriers only and the carriers consist of conductive material, each carrier is integral with one of the conductors and those portions of the carriers which contact the electrolyte constitute two electrodes which are conductively connected with the respective conductors. The configuration of the electrolyte between the carriers depends on the shape of carriers, on the distance between the carriers and/or the viscosity of electrolyte.

19 Claims, 29 Drawing Figures

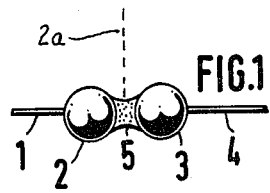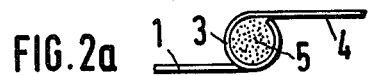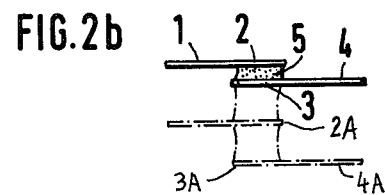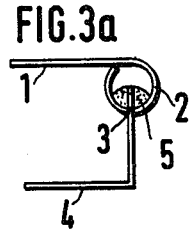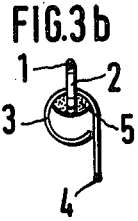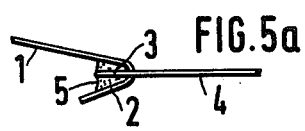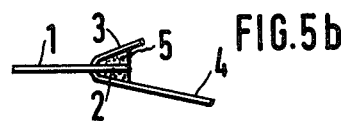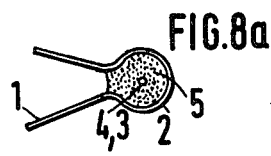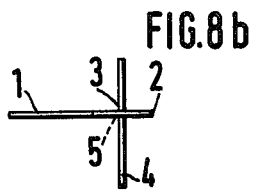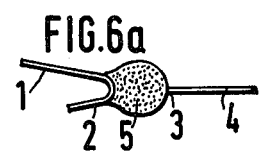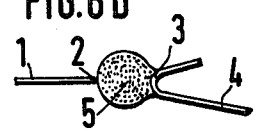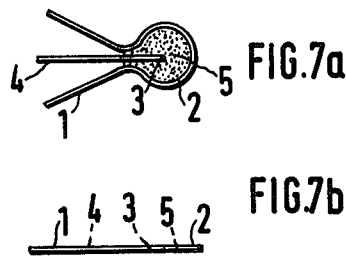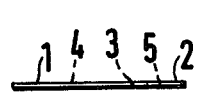

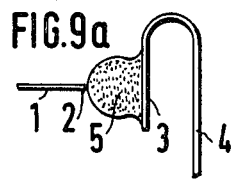
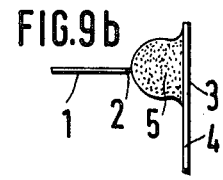
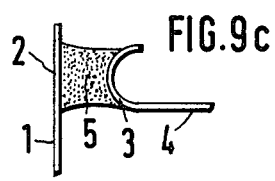
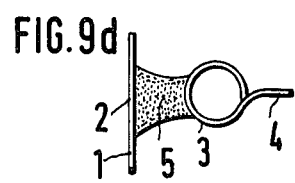
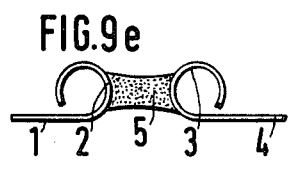
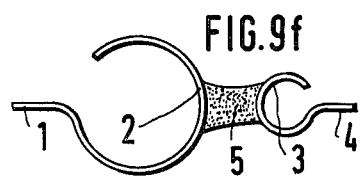
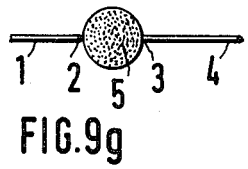
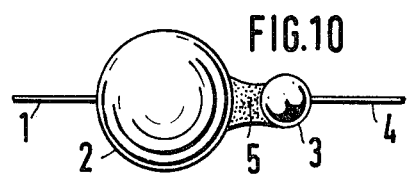
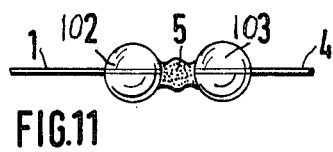

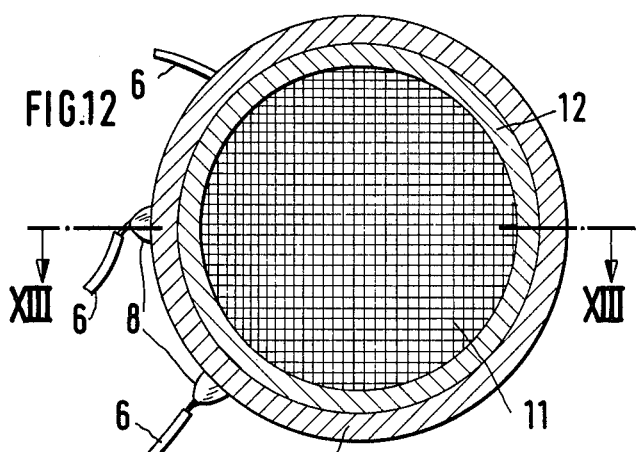
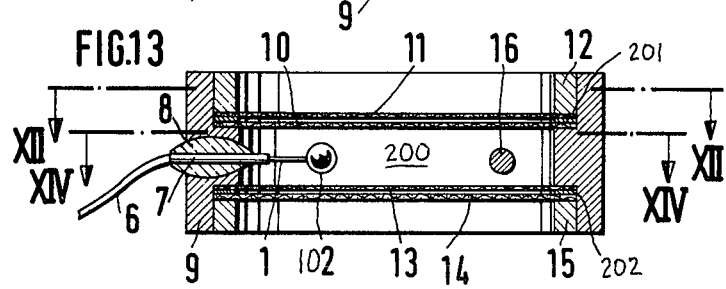
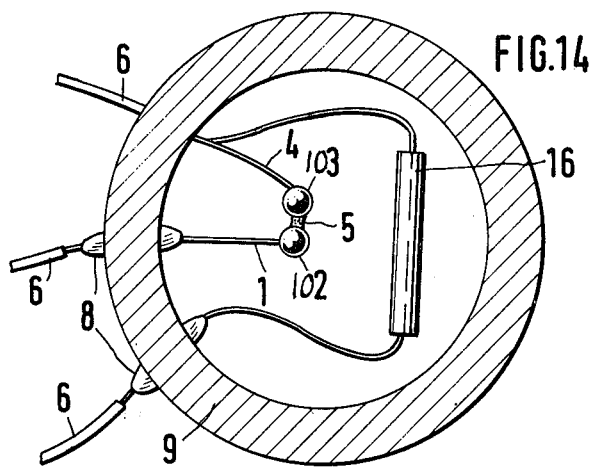

ELECTRIC HYGROMETER

BACKGROUND OF THE INVENTION

The present invention relates to electric hygrometers in general, and more particularly to improvements in the manner of and means for supporting the electrolyte in electric hygrometers.

Electric hygrometers are used for determination of relative humidity of gaseous fluids. In such hygrometers, a body of electrolyte is supported between conductors which are connected in circuit with a gauge, a transducer and/or other components of the instrument. The electrolyte is hygroscopic and the impedance between the electrodes is indicative of the relative humidity. The electrolyte is contacted by the electrodes which may constitute portions of the conductors or portions of the supporting or carrier means. For the sake of consistency, the following description of the invention will denote as electrodes those conductive parts which are in actual contact with the electrolyte and through which electric current flows from a conductor to the electrolyte or vice versa, i.e., through which current flows from a first type to a different second type of conductive material.

It is known to measure the relative humidity of air or another gaseous fluid as well as the relative equilibrium humidity of substances other than gases by monitoring the impedance of a hydroscopic electrolyte which is applied to an insulating carrier, e.g., a carrier consisting of glass, ceramic material, textile material, paper or the like. The force with which the electrolyte is held in requisite position depends on the absorbency of the carrier meterial and/or the capillary force. If the electrolyte can be used in solid state, it is often deposited on the carrier means in the form of a thin film or layer.

The hygroscopicity of electrolyte enables the latter to assume a state of water vapor equilibrium with the surrounding atmosphere (air), with another gaseous medium, or with the adjacent stratum or strata of a non-gaseous substance which can absorb water vapors. The electrolyte accepts or releases water vapors until it assumes or reaches a state of equilibrium with the material or substance around it. Of course, it is also necessary to monitor and to take into consideration eventual changes in temperature of electrolyte and/or its carrier means because any deviations of temperature of electrolyte and especially of temperature of the carrier means from the temperature of the surrounding medium greatly affect the accuracy of measurement of relative humidity.

As a rule, the electrodes of presently known hygrometers are applied directly to the carrier means for the electrolyte. Reference may be had to Swiss Pat. No. 382,465. The hygrometer which is disclosed in this patent exhibits a serious drawback, namely, that its reaction to changes in climatic conditions (changes in relative humidity which are normally accompanied by temperature changes) is very slow. The thermal inertia of electrolyte, of electrolyte carrier and of other metallic and/or plastic parts of the patented hygrometer causes a rather long delay between the instant of temperature change and the time when the temperature of component parts of the hygrometer changes sufficiently to conform to the changed temperature of the monitored medium. Consequently, the indications of relative humidity are inaccurate for a certain interval of time in response to each and every temperature change.

SUMMARY OF THE INVENTION

An object of the invention is to provide an electric hygrometer with novel and improved means for supporting the electrolyte, with novel and improved means for imparting to the electrolyte an optimum size and/or shape, and with novel and improved means for rendering the electrolyte shock- and vibration-resistant.

Another object of the invention is to provide a hygrometer which can respond to and account for changes in the temperature of the monitored medium (e.g., a gas) within a fraction of time which is needed in conventional hygrometers.

A further object of the invention is to provide a novel and improved miniature hygrometer whose accuracy is not affected by its minute size.

An additional object of the invention is to provide an electric hygrometer which can utilize any conventional hygroscopic electrolyte and wherein the electrolyte can be held and maintained in an optimum position of contact with the electrodes even if the mounting of its carrier means varies pronouncedly from hygrometer to hygrometer.

The invention is embodied in an electric hygrometer, particularly for measurement of relative humidity of gaseous media. The hygrometer comprises spaced apart first and second conductors (e.g., platinum wires or other noble metal wires having a diameter which is a fraction of one millimeter), a body of hygroscopic electrolyte intermediate the conductors, and means for supporting the electrolyte in moisture-exchanging contact with the medium whose relative humidity requires determination and in conductive contact with the conductors whereby the impedance between the conductors varies with relative humidity of the medium. In accordance with a feature of the invention, the supporting means comprises a plurality of spaced-apart electrolyte carriers and the carriers constitute the sole means for maintaining the electrolyte in contact with the conductors, i.e., a portion of the electrolyte is invariably suspended between two or more spaced-apart carriers. The hygrometer further comprises first and second electrodes which are electrically connected with the respective (first and second) conductors and contact spaced-apart portions of the electrolyte which is supported by and suspended between the carriers. If at least one of the carriers consists of a conductive material (e.g., platinum wire or another noble metal wire), one of the electrodes may form part of such conductive carrier. The carriers may be straight or looped wires, U-shaped or V-shaped wires, open or closed rings or spheres consisting of insulating or metallic material. Ring-shaped, U-shaped or V-shaped carriers may but need not be interlaced with each other (i.e., one thereof may extend into the space within the other without, however, actually contacting the other carrier). Also, ring-shaped, U-shaped, V-shaped or straight wire-like carriers may but need not be located in a common plane.

The novel features which are considered as characteristic of the invention are set forth in particular in the appended claims. The improved hygrometer itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 1 is a schematic elevational view of a portion of an electric hygrometer wherein the carriers for a hygroscopic electrolyte are constructed and assembled in accordance with a first embodiment of the invention;

FIG. 2a is a plan view of a portion of a hygrometer with a set of modified electrolyte carriers;

FIG. 2b is a side elevational view of the structure shown in FIG. 2a;

FIG. 3a is a first view of a portion of a hygrometer having interlaced ring-shaped electrolyte carriers;

FIG. 3b is a different view of the structure shown in FIG. 3a;

FIG. 4a is a first view of a portion of a hygrometer having U-shaped electrolyte carriers;

FIG. 4b is a different view of the structure shown in FIG. 4a;

FIG. 5a is a first view of a portion of a hygrometer with V-shaped electrolyte carriers;

FIG. 5b is a different view of the structure shown in FIG. 5a;

FIGS. 6a and 6b are two different views of a modification of the hygrometer with V-shaped electrolyte carriers;

FIGS. 7a and 7b are two different views of a portion of a hygrometer having a looped and a straight electrolyte carrier;

FIGS. 8a and 8b are two different views of a modification of the structure shown in FIGS. 7a and 7b;

FIG. 9a illustrates a modification of the structure which is shown in FIGS. 7a–7b or 8a–8b;

FIG. 9b shows a modification with two straight wire-like electrolyte carriers;

FIG. 9c shows a further modification of the structure which is illustrated in FIGS. 7a–7b, 8a–8b or FIG. 9a;

FIG. 9d shows a modification of the embodiment which is illustrated in FIG. 9c;

FIG. 9e shows a modification of the embodiment of FIG. 1;

FIG. 9f shows a modification of the embodiment of FIG. 9e;

FIG. 9g shows a modification of the embodiment of FIG. 9b;

FIG. 10 shows a modification of the embodiment of FIGS. 1, 9e and 9f;

FIG. 11 shows another modification of the embodiment of FIG. 1;

FIG. 12 is a sectional view of the housing of a hygrometer which embodies the invention, as seen in the direction of arrows from the line XII—XII of FIG. 13;

FIG. 13 is an axial sectional view as seen in the direction of arrows from the line XIII—XIII of FIG. 12;

FIG. 14 is a sectional view as seen in the direction of arrows from the line XIV—XIV of FIG. 13;

DESCRIPTION OF THE PREFERRED EMBODIMENTS

Figure 15:
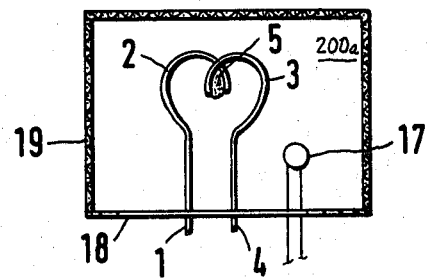
FIG. 15 is a fragmentary axial sectional view of a modified housing.

FIG. 1 shows a portion of a hygrometer which comprises two conductors 1, 4, two spherical electrolyte carriers 2, 3 which are respectively connected to the conductors 1, 4, and a body 5 of hygroscopic electrolyte between the carriers 2, 3. The carriers 2, 3 consist of conductive material and those portions thereof which contact the electrolyte 5 constitute the electrodes. The distance between the carriers 2, 3 is preferably between $0.05r$ and $r$ wherein $r$ is the radius of a carrier.

The electrolyte 5 is suspended in space between the carriers 2, 3 and its dimensions as well as shape depend on cohesion and adhesion between its material and the material of the carriers. If desired or necessary, the hygrometer which embodies the structure of FIG. 1 may include more than two electrolyte carriers one of which is shown by broken lines, as at 2a. The carrier 2a is a wire which is assumed to be located in a common plane with the conductors 1, 4 and one end portion of which contacts and supports the electrolyte. A similar carrier can be provided at the opposite side of the electrolyte 5 in line with the carrier 2a. Additional carriers can be provided in a plane which is normal to the plane of FIG. 1 and includes the carrier 2a; each such additional carrier may extend radially of the electrolyte 5. The overall number of carriers (the minimal number is two) depends on the intended use of the hygrometer and the desired size or volume of the electrolyte, i.e., the electrolyte is less likely to leave the space between the spherical carriers 2, 3 if the overall number of carriers exceeds two. In other words, the hygrometer can stand more pronounced shaking and other forces if the electrolyte 5 is contacted by a large number of carriers. The additional carriers may but need not consist of a conductive material.

Other components of the hygrometer which embodies the structure of FIG. 1 will be described in connection with FIGS. 12–14 and 16. Electrolyte which can be utilized in the hygrometer of the present invention are described, for example, in Swiss Pat. No. 382,465 and in an article by A. Wexler entitled "Electric Hygrometers" and published in Circular No. 586 by the National Bureau of Standards (Sept. 3, 1957).

FIGS. 2a and 2b show a portion of a second hygrometer. All such parts of the second hygrometer which are identical with or clearly analogous to the corresponding parts of the first hygrometer are denoted by similar reference characters. The carriers 2, 3 of FIGS. 2a and 2b are rings which are integral with the respective conductors 1, 4. Each of these carriers may constitute a suitably deformed end portion of the respective conductor. In contrast to the embodiment of FIG. 1 (wherein only a portion of each spherical carrier constitutes an electrode), each of the ring-shaped carriers 2, 3 of FIGS. 2a and 2b constitutes, in its entirety, an electrode.

The carriers 2, 3 are disposed in parallel planes (see FIG. 2b) and are coaxial with each other. The electrolyte 5 resembles a disk which is disposed between the two carriers. Here, too, the configuration and volume of the electrolyte 5 depend on cohesion and adhesion between its material and the material of the ring-shaped carriers. The conductors 1, 4 of FIGS. 1, 2a, 2b may consist of platinum wire having a diameter which is a small fraction of one millimeter, e.g., 0.1 millimeter.

FIG. 2b shows two additional ring-shaped carriers 2A, 3A (indicated by phantom lines). If the hygrometer includes all four carriers (2, 2A, 3, 3A) of FIG. 2b, the volume of the electrolyte is increased accordingly. At least one of the additional carriers 2A, 3A may (but need not) constitute an electrode. For example, the carriers 2 and 3A may constitute electrodes. The electrolyte 5 then establishes an electrical connection between the conductors 1 and 4A.

FIGS. 3a and 3b show two conductors 1, 4 whose end portions 2, 3 constitute two ring-shaped or eyeletshaped carriers for a body of electrolyte 5. The carrier 3 is smaller than the carrier 2 and the two carriers are out of direct contact with each other, the same as in all other embodiments of the invention. The conductors 1, 4 and their carriers 2, 3 (each of which constitutes an electrode) consist of platinum wire having a diameter of 0.1 millimeter. The electrolyte 5 is suspended in space between the carriers 2, 3. The carriers can extend into each other (i.e., they can be interlaced) but are invariably out of direct contact.

FIGS. 4a and 4b show the conductors 1, 4, the electrolyte carriers 2, 3 and the electrolyte 5 of a further hygrometer. The carriers 2, 3 are U-shaped and form integral parts of the respective conductors 1, 4. The carrier 2 extends into the space which is surrounded by the carrier 3 and vice versa, i.e., the carriers can be said to be interlaced, but they do not contact each other. Each carrier constitutes an electrode which contacts the electrolyte.

FIGS. 5a and 5b illustrate a portion of a hygrometer which is practically identical with that of FIGS. 4a and 4b except that the conductors 1, 4 are integral with V-shaped electrodes 2, 3 which constitute carriers for the electrolyte. The carriers or electrodes are interlaced or interlinked but do not touch each other. The electrolyte 5 between the V-shaped carriers of FIGS. 5a and 5b is smaller than the electrolyte between the U-shaped carriers of FIGS. 4a and 4b, even though the distance between the V-shaped carriers is the same as that between the U-shaped carriers. This is attributable to the smaller radii of curvature of the webs or bights of the V-shaped carriers.

Referring to FIGS. 6a and 6b, the carriers 2, 3 for the electrolyte 5 are V-shaped electrodes which are integral with the respective conductors 1, 4. The difference between the embodiments of FIGS. 5a-5b and 6a-6b is that the carriers of FIGS. 6a-6b are not interlinked, i.e., their bights are adjacent to but spaced apart from each other and their flanges or legs extend in the opposite directions. The plane of the carrier 2 is normal to the plane of the carrier 3.

The electrolyte carriers may (but need not) be interlaced with each other in each and every embodiment of the improved hygrometer, provided that the configuration of the carriers (see FIG. 1) allows for such interlacing. The distance between the carriers cannot be increased at will, i.e., its maximum value is determined by the ability of the electrolyte to adhere to the carriers. The distance can be increased if the electrolyte is supported by three or more carriers. It has been found that interlaced carriers (such as those shown in FIGS. 3a-3b, 4a-4b and 5a-5b) are better suited to hold the electrolyte even if the housing of the hygrometer is subjected to pronounced shaking or other mechanical stresses which tend to separate the electrolyte from its carriers.

FIGS. 7a and 7b show a portion of a hygrometer wherein the carrier 2 is a loop which is integral with the conductor 1 and the carrier 3 constitutes the straight end portion of the conductor 4. The conductors 1, 4 and their carriers 2, 3 are located in a common plane (see FIG. 7b) and, therefore, the electrolyte 5 is a flat body which is located within the confines of the looped carrier 2 and into which the carrier 3 extends. It will be noted that the carriers 2 and 3 do not touch each other.

FIGS. 8a and 8b show a modification of the structure of FIGS. 7a and 7b. The conductor 4 and its carrier 3 are normal to the plane of the looped carrier 2 which is integral with the conductor 1. The straight carrier 3 traverses the flat electrolyte 5 which is confined by the looped carrier 2.

FIG. 9a shows a portion of a further hygrometer wherein the carrier 2 constitutes the straight end portion of the conductor 1 and the carrier 3 is a U-shaped body one leg or flange of which is integral with the conductor 4. The electrolyte 5 is a flat or nearly flat body which is disposed between the other (left-hand) leg or flange of the carrier 3 and the straight carrier 2. The carriers 2, 3 and the conductors 1, 4 consist of a thin metallic wire (preferably platinum wire) and the carriers 2, 3 do not touch each other. Those portions of the carriers which contact the electrolyte constitute the electrodes. The parts 1, 2, 3, 4 are located in a common plane.

FIG. 9b shows two conductors 1, 4 which make a right angle and whose straight end portions 2, 3 constitute the carriers for a flat electrolyte 5. The electrolyte 5, the illustrated portions of the conductors 1, 4 and the carriers 2, 3 are located in a common plane (i.e., in the plane of FIG. 9b). The carriers 2, 3 do not touch each other.

FIG. 9c shows a first conductor 2 with a straight carrier 2 and a second conductor 4 with a U-shaped carrier 3. The electrolyte 5 is disposed between the carrier 2 and the outer side of the carrier 3, i.e., it adheres to the convex side of the latter carrier. The carriers 2 and 3 are disposed in a common plane and do not touch each other.

FIG. 9d shows a structure which is identical with that of FIG. 9c, except that the carrier 3 is a ring which is integral with the respective conductor 4. The conductor 1 and its straight end portion or carrier 2 are spaced apart from, coplanar with, and substantially tangential to the ring-shaped carrier 3.

In the embodiment of FIG. 9e, the carriers 2 and 3 are integral with the respective conductors 1, 4 and are disposed in a common plane. Each carrier is or closely approximates a ring and the electrolyte 5 is a substantially flat body which extends between the carriers. Those portions of the carriers which contact the electrolyte 5 constitute the electrodes. It will be noted that the electrolyte contacts the convex outer sides of the carriers.

The structure of FIG. 9f differs from the embodiment of FIG. 9e in that the diameter of the carrier 2 greatly exceeds the diameter of the carrier 3.

In the embodiment of FIG. 9g, the carriers 2 and 3 are coaxial wires which constitute the end portions of the respective conductors 1, 4. The electrolyte 5 between the straight carriers 2, 3 is normally a spherical or drop-shaped body.

FIG. 10 shows a further embodiment which differs from the structure of FIG. 9f in that each carrier 2, 3 is a circumferentially complete circle. The radii of curvature of the carriers (or of the curved portions of the carriers) may vary within a wide range, and the same applied for the diameters of spherical carriers. In some instances, the range of acceptable radii of curvature or diameters is limited by the nature of the procedure which is resorted to for the making of the carriers and/or by the viscosity of electrolyte. The stability of the hygrometer (i.e., the ability of the electrolyte to adhere to the carriers in spite of shaking and/or other mechanical stresses) depends on the distance between the carriers, the viscosity of the electrolyte, the dimensions and shape of the carriers, as well as whether or not the carriers are interlaced with each other.

In each of the heretofore described embodiments, the carriers are conductive and constitute or include electrodes which contact the electrolyte. FIG. 11 shows an embodiment wherein the spherical carriers 102, 103 consist of glass or other suitable insulating material and are surrounded and/or traversed by ring-shaped or straight end portions of the respective conductors 1, 4. Those parts of such straight or ring-shaped portions which contact the electrolyte 5 constitute the electrodes.

The structure of FIG. 11 resembles the embodiment of FIGS. 1 or 9g. However, it exhibits an important advantage which is not shared by the structure of FIG. 9g, namely, proper selection of the distance between the spherical insulating carriers 102, 103 is less critical than that between the carriers 2, 3 of FIG. 9g. The same applies for other parameters as regards the positioning of carriers relative to each other, i.e., it is desirable that the carrier 2 of FIG. 9g be exactly coaxial with the carrier 3. On the other hand, the conductors 1, 4 of FIG. 11 may but need not be coaxial with each other, i.e., the center of the spherical carrier 102 can be located in front of or behind the plane of FIG. 11 if the center of the carrier 103 is located in such plane, or vice versa.

As mentioned hereinabove, the number of carriers can be increased to three, four or more (regardless of whether the carriers are straight or bent wires, spherical or polygonal bodies, other configurations or combinations of these) and all carriers may but need not be of identical size and/or shape. The number of carriers is preferably increased when the hygrometer is expected to be subjected to pronounced shaking or other mechanical stresses which would tend to terminate the bond between the electrolyte and the electrodes.

It is further within the purview of the invention to utilize conductors and/or electrodes in the form of thin metallic films, strips or layers which are applied to thin glass filaments, e.g., galvanically or by resorting to another known coating technique. Thus, and referring to FIG. 11 by way of example, each of the conductors 1 and 4 may include a filament consisting of an insulating material and a strip of metallic material which contacts the electrolyte 5 and is in circuit with certain other components of the hygrometer.

The radii of curvature of U-shaped or V-shaped carriers are preferably in the range between 0.05 and 0.5 millimeter if the carriers consist of a metallic wire (preferably platinum wire) with a diameter in the range of 0.1 millimeter.

The heretofore described parts of the hygrometer are preferably installed in a housing or casing, for example, in a manner as shown in FIGS. 12, 13 and 14. The housing must be provided with fluidproof passages for the conductors 1 and 4, and the conductors (or their conductive strips or films) must be insulated from the housing.

FIGS. 12-14 show that the housing comprises an annular frame member 9 which is open at both ends and confines pairs of parallel foraminous walls or screens 10, 11 and 13, 14 which form a chamber 200 for the electrolyte 5 and its carriers 2, 3. The screens 10, 11 and 13, 14 are respectively separated from each other by ring-shaped distancing members 201, 202. The frame member 9 may be provided with internal threads to mesh with the external threads of washer-like retaining elements 12, 15 which are respectively adjacent to the marginal portions of the screens 11 and 14. Alternatively, each of the elements 12, 15 can be a press-fit in or glued to the frame member 9.

The screens 10, 11, 13, 14 allow for uniform diffusion of moisture in the chamber 200. They are preferably designed to intercept dust or other solid particulate material and preferably also to intercept substances which would react with the material of the electrolyte 5 in the chamber 200.

The spherical electrolyte carriers 102, 103 (see FIG. 14) are assumed to be identical with the carriers of FIG. 11. The conductors 1, 4 have circular end portions which surround the respective spherical carriers and parts of which constitute electrodes in contact with the electrolyte 5. The conductors 1, 4 form part of two cables 6 which are located at the outside of the housing including the frame member 9 and walls or screens 10, 11, 13 and 14. Each of the conductors 1, 4 passes through and is soldered to a small-diameter metallic pipe 7 which extends through a tubular glass insulator 8 embedded in the frame member 9. The insulators 8 can be omitted if the frame member 9 consists of insulating material (e.g., a suitable synthetic plastic substance).

The material and other features (such as mesh) of the screens 10, 11, 13 and 14 form no part of the invention. Such screens are known in the art of electric hygrometers. The retaining elements 12, 15 may consist of a metallic, synthetic plastic or other suitable material, the same as the distancing rings 201 and 202.

The chamber 200 further receives a resistor 16 whose resistance varies as a function of changes in temperature of gaseous fluid which fills the interior of the housing. The resistor 16 can be used for measurement of temperature and/or as a means which automatically compensates for changes in temperature in a manner known from the art of hygrometers.

It is clear that the housing of FIGS. 12 to 14 may include only two or three screens, or more than four screens. For example, the chamber 200 can be disposed between two or three screens (10, 13 or 10, 14 or 11, 13 or 11, 14 or 10, 13, 14 or 11, 13, 14 or 10, 11, 13 or 10, 11, 14). The screens 10, 11 or 13, 14 can be replaced with a hermetically sealing disk (not shown) which allows air or another moisture carrying medium to enter the chamber 200 at the one or the other axial end of the frame member 9. This is sufficient or desirable when the hygrometer is used to measure relative moisture in the gaseous fluid at one side of a flat body.

FIG. 15 shows a modified hygrometer wherein the housing includes a plate-like holder 18 and a fine-mesh screen 19 which surrounds the carriers 2, 3, the electrolyte 5 between the carriers and a thermistor 17 or another suitable semiconductor which replaces the temperature-responsive resistor 16 of FIG. 14. The screen 18 constitutes a thermodynamic coupling between th surrounding atmosphere and the parts which are confined in the chamber 200a defined by the housing 18, 19. The structure of FIG. 15 is small enough to resemble the head or the point of a needle the longer portion of which extends downwardly, as viewed in the drawing, and accommodates other components of the hygrometer.

Since an electric hygrometer is temperature sensitive, it normally comprises a temperature-responsive reference resistor, such as the element 16 of FIGS. 13-14, the element 17 of FIG. 15, or a hygrometer cell which is hermetically sealed in a compartment wherein the humity remains constant. The compartment contains a tissue which is saturated with a salt solution. Special measures must be undertaken to avoid any contact between the tissue and the electrolyte and/or any contact between the tissue and the cell which contains the electrolyte.

The just mentioned tissue and the precautionary measures which must be undertaken due to utilizatiion of such tissue can be dispensed with if the conditioning of the hermetically sealed compartment is effected by resorting to a suitable salt solution and the solution is supported by carriers which are constructed and/or configured in the same way as the carriers of the improved hygrometer. If the compartment is large enough, it can accommodate two or more sets of carriers. The second (reference) cell is then identical with a cell which contains the electrolyte (i.e., with a cell which is used for actual measurement of relative humidity), except that it is confined in the hermetically sealed compartment which is conditioned by the salt solution. The solution in the compartment may be identical with the electrolyte in the humidity measuring cell. This brings about the advantage that the influence of temperature changes on all physical parameters at the measuring and reference sides of the apparatus is the same, i.e., that the compensation for temperature changes is ideal.

Figure 16:
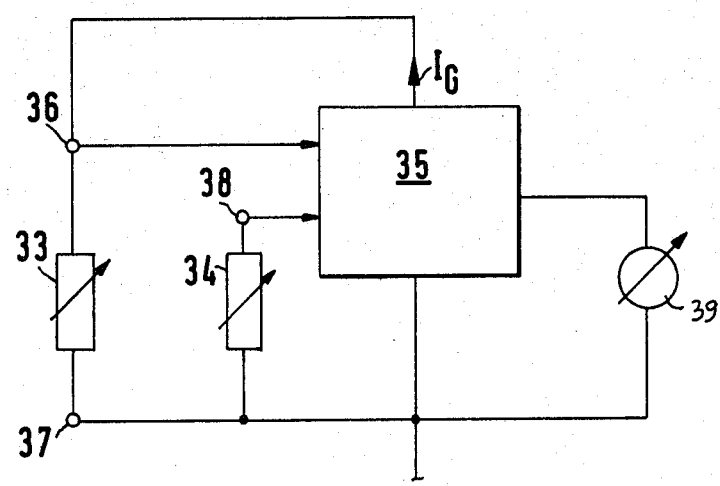
FIG. 16 is the circuit diagram of a hygrometer which embodies the invention.

FIG. 16 is a circuit diagram of a hygrometer which embodies the invention. The reference character 33 denotes a variable impedance (e.g., the electrolyte 5 of FIG. 1), the reference character 34 denotes a temperature-responsive resistor (e.g., the resistor 16 of FIG. 14) and the conductors 36, 37 correspond to the conductors 1, 4 of FIG. 1. The circuit further includes a transducer 35 which is connected with the conductors 36, 37 as well as with the conductor 38 for one end of the resistor 34. The other end of the resistor 34 is connected with the conductor 37. The gauge 39 is connected between the conductor 37 and the output of the transducer 35. The reference character $I_G$ denotes the connection between the transducer 35 and a source of generator current.

The circuit of FIG. 16 is but one example of circuits which can utilize an electrolyte mounted on or supported solely by two or more carriers in a manner as disclosed in connection with FIGS. 1 to 15. The exact nature of circuitry in the improved hygrometer, save for the components shown in FIGS. 1 to 15, forms no part of the invention.

Many advantages of the improved hygrometer have been pointed out hereinabove. In addition, the hygrometer exhibits the following important features. The size and/or shape of the electrolyte, its carriers and electrodes can be varied within an extremely wide range, e.g., in dependency on the type of available machinery, the selected or desirable chemical composition of the electrolyte, the desired size of the housing and/or other parameters. This, in turn, renders it possible to influence the operation of the hygrometer within a wide range. Also, the true resistance of the impedance can have a very low ohmic value. Therefore, the improved hygrometer can be designed to conform optimally to the associated electrical and/or electronic components. Still further, the versatility of the improved instrument greatly exceeds that of conventional electric hygrometers.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

What is claimed is:

1. In an electric hygrometer, particularly for measurement of relative humidity of gaseous media, a combination comprising spaced-apart first and second conductors; a body of liquid hygroscopic electrolyte intermediate said conductors; and means for supporting the electrolyte in moisture-exchanging contact with a medium whose relative humidity requires determination and in conductive contact with said conductors whereby the impedance between said conductors varies with relative humidity of said medium, said supporting means comprising a plurality of spaced-apart electrolyte carriers and said carriers constituting the sole means for maintaining the electrolyte in suspended condition therebetween and in conductive contact with said conductors.

2. A combination as defined in claim 1, further comprising first and second electrodes electrically connected with the respective conductors and contacting spaced-apart portions of said electrolyte, at least one of said electrodes forming part of one of said carriers.

3. A combination as defined in claim 1, wherein said carriers include first and second carriers which consist of wire and are integral with the respective conductors, at least one of said first and second carriers having a configuration which deviates from a straight line and being located in a predetermined plane, the other of said first and second carriers being coplanar with said one carrier.

4. A combination as defined in claim 1, wherein the number of said carriers exceeds two.

5. A combination as defined in claim 4, wherein said carriers include first and second carriers which are respectively connected with said first and second conductors.

6. A combination as defined in claim 1, wherein said carriers include coaxial straight first and second carriers which are respectively connected with said first and second conductors, said carriers consisting of metallic wire.

7. In an electric hygrometer, particularly for measurement of relative humidity of gaseous media, a combination comprising spaced-apart first and second conductors; a body of hygroscopic electrolyte intermediate said conductors; and means for supporting the electrolyte in moisture-exchanging contact with a medium whose relative humidity requires determination and in conductive contact with said conductors whereby the impedance between said conductors varies with relative humidity of said medium, said supporting means comprising a plurality of spaced-apart electrolyte carriers and said carriers constituting the sole means for maintaining the electrolyte in conductive contact with said conductors, said carriers including first and second spherical carriers electrically connected with the respective conductors.

8. In an electric hygrometer, particularly for measurement of relative humidity of gaseous media, a combination comprising spaced-apart first and second conductors; a body of hygroscopic electrolyte intermediate said conductors; and means for supporting the electrolyte in moisture-exchanging contact with a medium whose relative humidity requires determination and in conductive contact with said conductors whereby the impedance between said conductors varies with relative humidity of said medium, said supporting means comprising a plurality of spaced-apart electrolyte carriers and said carriers constituting the sole means for maintaining the electrolyte in conductive contact with said conductors, said carriers including coaxial first and second ring-shaped carriers which are electrically connected with the respective conductors.

9. A combination as defined in claim 8, wherein said ring-shaped carriers have identical diameters.

10. In an electric hygrometer, particularly for measurement of relative humidity of gaseous media, a combination comprising spaced-apart first and second conductors; a body of hygroscopic electrolyte intermediate said conductors; and means for supporting the electrolyte in moisture-exchanging contact with a medium whose relative humidity requires determination and in conductive contact with said conductors whereby the impedance between said conductors varies with relative humidity of said medium, said supporting means comprising a plurality of spaced-apart electrolyte carriers and said carriers constituting the sole means for maintaining the electrolyte in conductive contact with said conductors, said carriers including interlaced first and second ring-shaped carriers which are integral with the respective conductors.

11. A combination as defined in claim 10, wherein said ring-shaped carriers consist of metallic wire.

12. In an electric hygrometer, particularly for measurement of relative humidity of gaseous media, a combination comprising spaced-apart first and second conductors; a body of hygroscopic electrolyte intermediate said conductors; and means for supporting the electrolyte in moisture-exchanging contact with a medium whose relative humidity requires determination and in conductive contact with said conductors whereby the impedance between said conductors varies with relative humidity of said medium, said supporting means comprising a plurality of spaced-apart electrolyte carriers and said carriers constituting the sole means for maintaining the electrolyte in conductive contact with said conductors, said carriers including interlaced first and second U-shaped carriers which are integral with the respective conductors.

13. In an electric hygrometer, particularly for measurement of relative humidity of gaseous media, a combination comprising spaced-apart first and second conductors; a body of hygroscopic electrolyte intermediate said conductors; and means for supporting the electrolyte in moisture-exchanging contact with a medium whose relative humidity requires determination and in conductive contact with said conductors whereby the impedance between said conductors varies with relative humidity of said medium, said supporting means comprising a plurality of spaced-apart electrolyte carriers and said carriers constituting the sole means for maintaining the electrolyte in conductive contact with said conductors, said carriers including interlaced first and second V-shaped carriers which are integral with the respective coductors.

14. In an electric hygrometer, particularly for measurement of relative humidity of gaseous media, a combination comprising spaced-apart first and second conductors; a body of hygroscopic electrolyte intermediate said conductors; and means for supporting the electrolyte in moisture-exchanging contact with a medium whose relative humidity requires determination and in conductive contact with said conductors whereby the impedance between said conductors varies with relative humidity of said medium, said supporting means comprising a plurality of spaced-apart electrolyte carriers and said carriers constituting the sole means for maintaining the electrolyte in conductive contact with said conductors, said carriers including first and second U-shaped or V-shaped carriers which are integral with the respective conductors and include convex outer sides facing each other.

15. In an electric hygrometer, particularly for measurement of relative humidity of gaseous media, a combination comprising spaced-apart first and second conductors; a body of hygroscopic electrolyte intermediate said conductors; and means for supporting the electrolyte in moisture-exchanging contact with a medium whose relative humidity requires determination and in conductive contact with said conductors whereby the impedance between said conductors varies with relative humidity of said medium, said supporting means comprising a plurality of spaced-apart electrolyte carriers and said carriers constituting the sole means for maintaining the electrolyte in conductive contact with said conductors, one of said carriers constituting a loop and being integral with one of said conductors and another of said carriers being a straight wire integral with the other of said conductors and extending with clearance into the interior of said loop.

16. A combination as defined in claim 15, wherein said loop is located in a predetermined plane and said other carrier is normal to said plane.

17. In an electric hygrometer, particularly for measurement of relative humidity of gaseous media, a combination comprising spaced-apart first and second conductors; a body of hygroscopic electrolyte intermediate said conductors; means for supporting the electrolyte in moisture-exchanging contact with a medium whose relative humidity requires determination and in conductive contact with said conductors whereby the impedance between said conductors varies with relative humidity of said medium, said supporting means comprising a plurality of spaced-apart electrolyte carriers and said carriers constituting the sole means for maintaining the electrolyte in conductive contact with said conductors, said carriers including first and second carriers which consist of insulating material; and first and second electrodes integral with the respective conductors and contacting the electrolyte in the region of said first and second carriers, respectively.

18. A combination as defined in claim 17, wherein said first and second carriers are spheres and said electrodes consist of wire.

19. A combination as defined in claim 17, wherein said first and second electrodes have portions which are respectively embedded in said first and second carriers.

* * * * *